United States Patent [19]

Shigehara et al.

[11] Patent Number: 5,023,336
[45] Date of Patent: Jun. 11, 1991

[54] IMIDAZOLE COMPOUND AND PROCESS FOR PREPARING THE SAME

[75] Inventors: Itaru Shigehara; Toshio Nakajima; Shigeyuki Nishimura; Takeshi Ohshima, all of Shiga, Japan

[73] Assignee: Ishihara Sangyo Kaisha Ltd., Osaka, Japan

[21] Appl. No.: 424,630

[22] Filed: Oct. 20, 1989

[30] Foreign Application Priority Data

Oct. 20, 1988 [JP] Japan ............................ 63-264868
Dec. 6, 1988 [JP] Japan ............................ 63-308678

[51] Int. Cl.$^5$ .................... C07D 233/68; C07D 233/90
[52] U.S. Cl. .................... 548/110; 548/337; 548/343
[58] Field of Search .............. 548/337, 341, 342, 343, 548/110

[56] References Cited

FOREIGN PATENT DOCUMENTS 0284828 10/1988 European Pat. Off. .
0298196 1/1989 European Pat. Off. .

OTHER PUBLICATIONS

Recueil Des Travaux Chimiques Des Pays-Bas, vol. 92, No. 3, 1973, pp. 449–459.
*Chemical Abstracts*, 109, 66336q (1988) (*Yakugaku Zasshi*, 108(4), 350–354, (1988)) Sagi et al.
*Chem. Parm. Bull.*, 31(12), 4549–4553 (1983) Yamanaka et al.
*Recl. Trav. Chim. Pays-Bas*, 92(3), 449–459 (1973) Lont et al.
*J. Org. Chem.*, vol. 38, No. 7, 1437–1438 (1973) Oliver et al.

*Primary Examiner*—John M. Ford
*Attorney, Agent, or Firm*—Sughrue, Mion, Zinn, Macpeak & Seas

[57] ABSTRACT

An imidazole compound is disclosed, which is represented by formula (I):

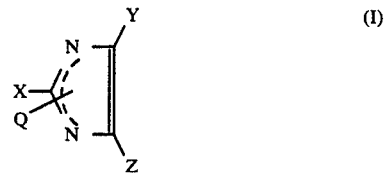

wherein:

X represents a —COOT group, in which T represents a hydrogen atom, an alkyl group, a benzyl group, or a phenyl group; or a —CONH$_2$ group, Y represents a hydrogen atom, a chlorine atom, or a bromine atom, Z represents an alkyl group containing from 2 to 6 carbon atoms, which may be substituted with one or more halogen atoms; or a phenyl group which may be substituted with one or more halogen atoms or alkyl groups, and Q represents a hydrogen atom; an —SO$_2$R$^1$ group, in which R$^1$ represents an alkyl group, a dialkylamino group, or a phenyl group which may be substituted with one or more alkyl groups; or a —CH(R$^2$)(R$^3$) group, in which R$^2$ represents a hydrogen atom, a methyl group, or an alkoxy group, and R$^3$ represents an alkoxy group, an —OCH$_2$CH$_2$Si (CH$_3$) group, or a phenyl group which may be substituted with one or more alkyl groups or alkoxy groups, provided that when Y and Q each represents a hydrogen atom and Z represents a phenyl group, X represents a group other than a —COOH-phenyl group, and a —CONH$_2$ group; and that when Y and Q each represents a hydrogen atom and Z represents an n—C$_5$H$_{11}$ group, X represents a group other than a —COOH group and a —COOC$_2$H$_5$ group.

Processes for preparing imidazole compounds are also disclosed.

The imidazole compounds are useful as an intermediate for production of biocides for controlling harmful organisms in the agricultural and horticultural areas, or medical and pharmaceutical fungicides.

2 Claims, No Drawings

IMIDAZOLE COMPOUND AND PROCESS FOR PREPARING THE SAME

The present invention relates to a novel imidazole compound which is useful as an intermediate for production of biocides for controlling harmful organisms in the agricultural and horticultural areas, or medical and pharmaceutical fungicides and to a process for preparing the same.

A number of imidazole compounds proposed so far are known. For example, *Chemical Abstracts*, 109, 66336q (1988) (*Yakugaku Zasshi*, 108(4), 350–354 (1988)) discloses 4(5)-pentylimidazole-2-carboxylic acid; *Chem. Parm. Bull.*, 31(12), 4549–4553 (1983) discloses ethyl 5-pentyl-2-imidazolecarboxylate and sodium 5-pentyl-2-imidazolecarboxylate; and *Recl. Trav. Chim. Pays-Bas*, 92(3), 449–459 (1973) discloses 4(5)-phenylimidazole-2-carboxylic acid and 2-carbamoyl-4(5)-phenylimidazole. For the preparation of imidazole compounds, for example, *J. Org. Chem.*, Vol. 38, No. 7, 1437–1438 (1973) discloses the following reaction scheme:

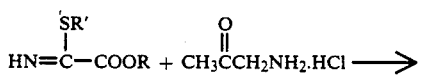

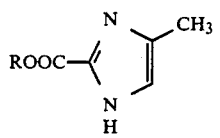

and *Chem. Pharm. Bull.*, 31(12), 4549–4553 (1983), as described above, discloses the following reaction scheme:

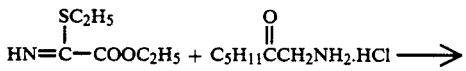

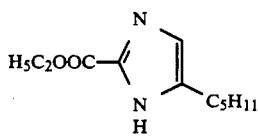

On the other hand, European Patent 298196A (Australian Unexamined Patent Publication No. 88/12883, published Sept. 15, 1988) discloses a general formula including a portion of the compounds of the present invention and generally discloses a method for preparing 2-carbamoylimidazole compounds which comprises reacting 2-methoxycarbonylimidazole compounds with ammonia. However, this patent does not disclose any operative example thereof.

That is, the present invention is concerned with an imidazole compound represented by formula (I):

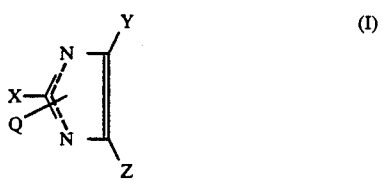

wherein:

X represents a —COOT group, in which T represents a hydrogen atom, an alkyl group, a benzyl group, or a phenyl group; or a —CONH$_2$ group, Y represents a hydrogen atom, a chlorine atom, or a bromine atom, Z represents an alkyl group containing from 2 to 6 carbon atoms, which may be substituted with one or more halogen atoms; or a phenyl group which may be substituted with one or more halogen atoms or alkyl groups, and Q represents a hydrogen atom; an —SO$_2$R$^1$ group, in which R$^1$ represents an alkyl group, a dialkylamino group, or a phenyl group which may be substituted with one or more alkyl groups; or a —CH(R$^2$)(R$^3$) group, in which R$^2$ represents a hydrogen atom, a methyl group, or an alkoxy group, and R$^3$ represents an alkoxy group, an —OCH$_2$CH$_2$Si(CH$_3$)$_3$ group, or a phenyl group which may be substituted with one or more alkyl groups or alkoxy groups, provided that when Y and Q each represents a hydrogen atom and Z represents a phenyl group, X represents a group other than a —COOH group, a —COOphenyl group, and a —CONH$_2$ group; and that when Y and Q each represents a hydrogen atom and Z represents an n—C$_5$H$_{11}$ group, X represents a group other than a —COOH group and a —COOC$_2$H$_5$ group.

In the definition for formula (I), examples of the alkyl group containing from 2 to 6 carbon atoms include an ethyl group, a propyl group, a butyl group, a pentyl group, and a hexyl group. These enumerated groups may be linear or have a side chain(s). Further, examples of the alkyl moiety constituting the alkyl group, dialkylamino group, alkoxy group, etc. include those containing from 1 to 6 carbon atoms, such as a methyl group, an ethyl group, a propyl group, a butyl group, a pentyl group, and a hexyl group. These enumerated groups may be linear or have a side chain(s). Examples of the halogen atom include a fluorine atom, a chlorine atom, a bromine atom, and an iodine atom. In the case that the number of the halogen atoms to be substituted on the alkyl group containing from 2 to 6 carbon atoms or the phenyl group is 2 or more, the halogen atoms may be the same as or different from each other.

In the definition for Q in formula (I), the —SO$_2$R$^1$ group and —CH(R$^2$)(R$^3$) group are generally used as protective groups, examples of which include those described in, for example, *J. Org. Chem.*, 53, 1107 (1988). Typical examples include a dimethylsulfamoyl group, a methanesulfonyl group, a benzenesulfonyl group, a 1-(1-ethoxyethyl) group, a dimethoxymethyl group, a diethoxymethyl group, a methoxymethyl group, a trimethylsilylethoxymethyl (SEM) group, and a benzyl group.

Among the imidazole compounds represented by formula (I), synthetically preferred compounds of the present invention are illustrated below.

(1) Compounds of formula (I) wherein X represents a —COOCH$_3$, a —COOC$_2$H$_5$ group or a —CONH$_2$ group.

(2) Compounds of formula (I) wherein Q represents a hydrogen atom.

The imidazole compound represented by formula (I) can, for example, be produced as Products (I-1) to (I-5) by the following Reaction Schemes (1) to (3).

Reaction Scheme (1)

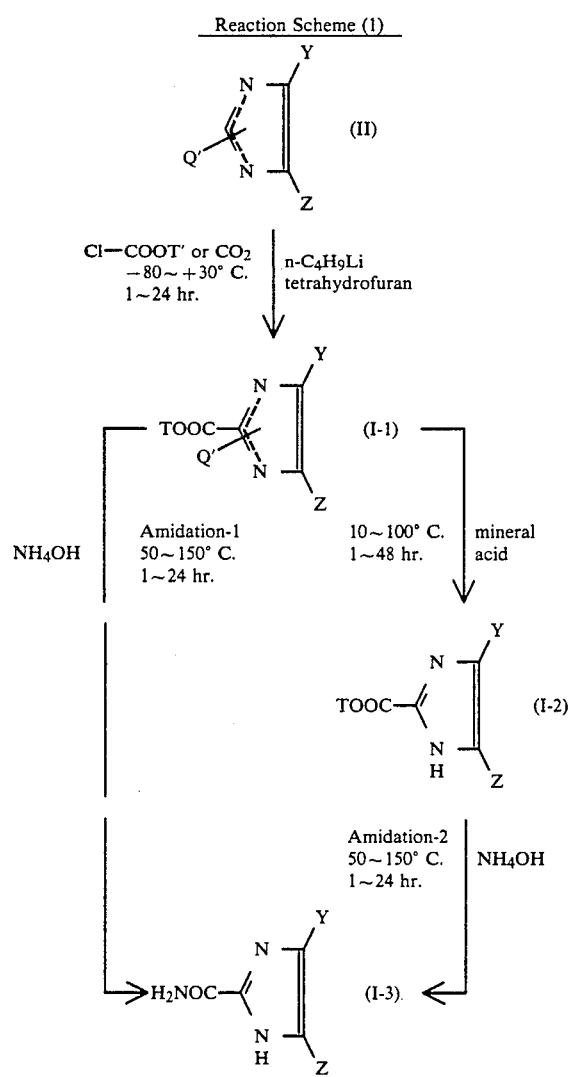

In the Amidation-1 of the Reaction Scheme (1), in the case that T in the compound represented by formula (I-1) represents a hydrogen atom, it is desired to produce a compound represented by formula (I-3) by the following Reaction Scheme (2).

Reaction Scheme (2)

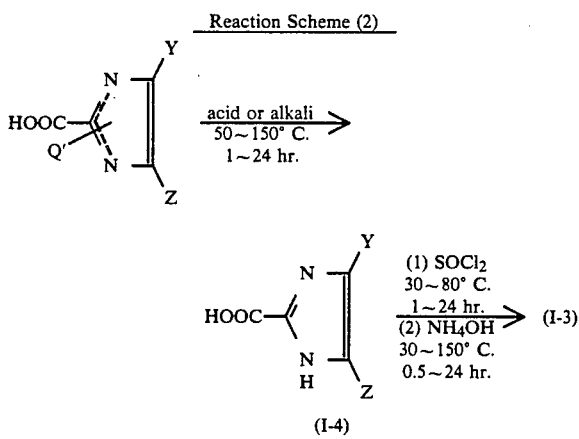

In the Reaction Scheme (1), a compound represented by formula (I-2) wherein Y represents a hydrogen atom, and T represents an alkyl group, a benzyl group, or a phenyl group can also be produced by the following Reaction Scheme (3).

Reaction Scheme (3)

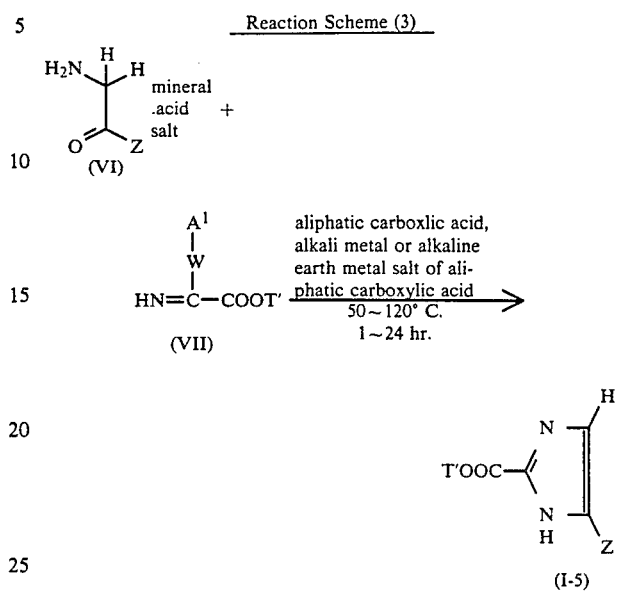

In the foregoing Reaction Schemes (1) to (3):

Q' represents an $-SO_2R^1$ group, in which $R^1$ represents an alkyl group, a dialkylamino group, or a phenyl group which may be substituted with one or more alkyl groups; or a $-CH(R^2)(R^3)$ group, in which $R^2$ represents a hydrogen atom, a methyl group, or an alkoxy group, and $R^3$ represents an alkoxy group, an $-OCH_2CH_2Si(CH_3)_3$ group, or a phenyl group which may be substituted with one or more alkyl groups or alkoxy groups, T' represents an alkyl group containing from 1 to 6 carbon atoms, a benzyl group, or a phenyl group, $A^1$ represents a methyl group or an ethyl group, W represents an oxygen atom or a sulfur atom and T, Y and Z are the same as defined above.

Among the compounds represented by formula (VII), compounds wherein W represents an oxygen atom are preferable for the reasons that the compounds can be prepared more easily that those wherein W represents a sulfur atom, as shown in the Reaction Scheme (5) described later and that the preparation method thereof does not give rise a bad smell and turbidity.

Examples of the mineral acid which is used in the Reaction Scheme (1) include hydrochloric acid and sulfuric acid. In the reaction for deriving the compound represented by formula (I-2) from the compound represented by formula (I-1), it is desired to use an alcohol such as methanol and ethanol. Further, in the Amidation-1 and Amidation-2, it is also desired to use such an alcohol.

In the Amidation-1 in the Reaction Scheme (1), though there is a possibility that the compound represented by formula (I-2) or a compound represented by formula (I-6) is formed during the reaction, it is not necessary to particularly isolate such a formed compound.

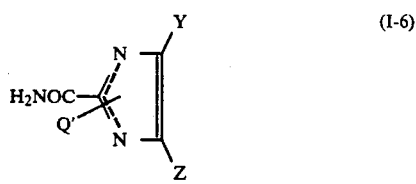

In formula (I-6), Q′, Y and Z are the same as defined above.

Further, in the compound represented by formula (I-2) or (I-3), in the case that Y represents a hydrogen atom, if desired, a reaction with a chlorinating agent or a brominating agent is carried out at −50° to +100° C. for 1 to 24 hours, whereby the compound can be converted into a compound wherein Y represents a chlorine atom or a bromine atom. This chlorination or bromination is carried out in the presence of a diluent, a neutralizing agent, etc., if desired. Examples of the diluent include those which are inert against the chlorinating agent or brominating agent, such as methylene chloride, chloroform, carbon tetrachloride, methanol, ethanol, acetic acid, and water. Examples of the neutralizing agent include sodium bicarbonate, sodium acetate, and sodium hydroxide.

In the Reaction Scheme (2), in the Reaction (2) for obtaining the compound represented by formula (I-3) from the compound represented by formula (I-4), it is desired to use such an alcohol as used in the Reaction Scheme (1), in addition to NH4OH.

Examples of the mineral acid salt of the compound represented by formula (VI) which is used in the Reaction Scheme (3) include hydrochloric acid salts and sulfuric acid salts.

In the Reaction Scheme (3), an aliphatic carboxylic acid and an alkali metal or alkaline earth metal salt of aliphatic carboxylic acid are used. Examples of the aliphatic carboxylic acid include acetic acid and propionic acid. Examples of the alkali metal or alkaline earth metal salt include salts of sodium, salts of potassium and salts of calcium.

In the Reaction Scheme (3), the compound represented by formula (VI) may be in the latent form of an acetal (sometimes called as a "ketal") or cyclic acetal represented by formula (VI′):

wherein A² and A³, which may be the same or different, each represents a methyl group, an ethyl group, an n-propyl group, or an isopropyl group; the adjacent —OA² group and —OA³ group may be taken together an —O(CH₂)ₘO— group, in which m represents an integer of from 2 to 4; and Z is the same as defined above.

In the Reaction Scheme (3), the mineral acid salt of the compound represented by formula (VI) can be, for example, produced by various methods shown in the following Reaction Scheme (4).

Reaction Scheme (4)

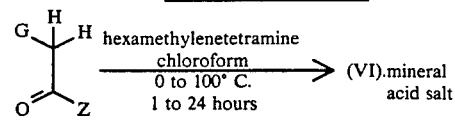

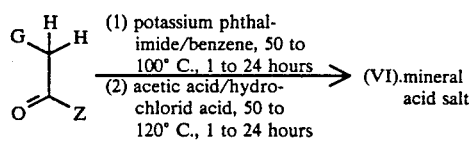

(C) The mineral acid salt of the compound represented by formula (VI) can be produced through

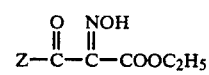

from

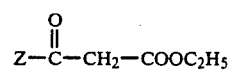

in the method described in *J. Amer. Chem. Soc.*, 2884 (1948).

In the Reaction Scheme (4), G represents a chlorine atom or a bromine atom, and Z is the same as defined above.

In addition, in the Reaction Scheme (3), the compound represented by formula (VII) can be produced by the following Reaction Scheme (5). The compound thus produced may be in the form of a mineral acid salt, an HBF₄ salt, or an HSO₃F salt. Examples of the mineral acid salt include hydrochloric acid salts, hydrobromic acid salts, and hydroiodic acid salts.

Reaction Scheme (5)

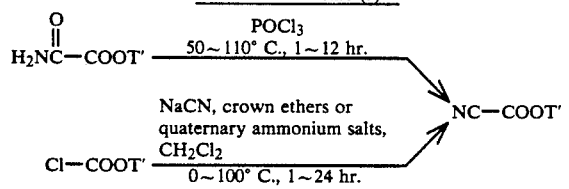

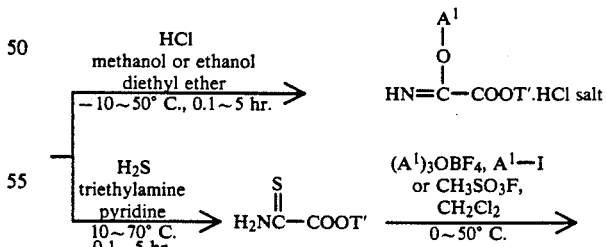

In the Reaction Scheme (5), T' and A¹ are the same as defined above. In the Reaction Scheme (5), the mineral acid salts which are not specifically described can be obtained in the same manner as in the case of those specifically described.

In the Reaction Scheme (1), the compound represented by formula (II) can be, for example, produced as the following Methods (A), (B) or (C) of Reaction Scheme (6).

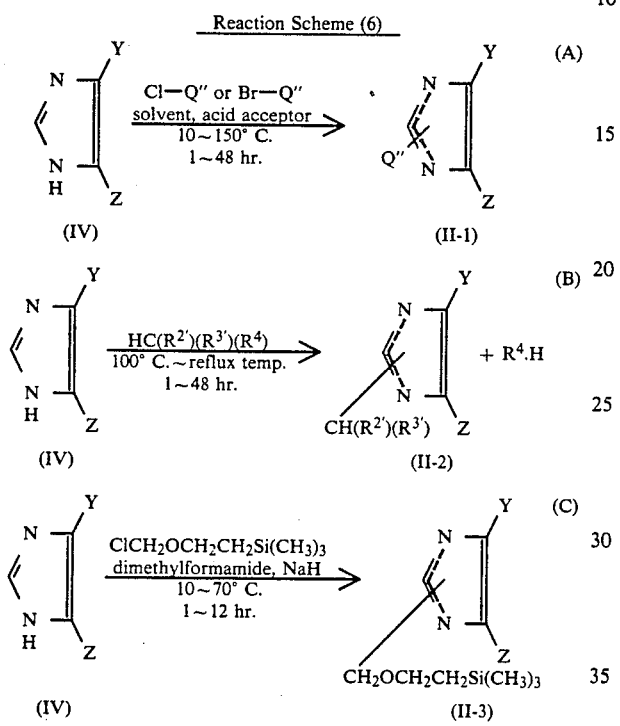

In the Reaction Scheme (6):

Q" represents an —$SO_2R^1$ group, in which $R^1$ represents an alkyl group, a dialkylamino group, or a phenyl group which may be substituted with one or more alkyl groups; or a —$CH(R^2)(R^3)$ group, in which $R^2$ represents a hydrogen atom, a methyl group, or an alkoxy group, and $R^3$ represents an alkoxy group, an —$OCH_2CH_2Si(CH_3)_3$ group, or a phenyl group which may be substituted with one or more alkyl groups or alkoxy groups, provided that $R^2$ and $R^3$ do not represent an alkoxy group at the same time, $R^{2'}$, $R^{3'}$, and $R^4$ independently represent an alkoxy group, and Y and Z are the same as defined above.

Examples of the solvent which can be used in the Reaction (A) above include aromatic hydrocarbons such as benzene, toluene, xylene, and chlorobenzene; cyclic or acyclic aliphatic hydrocarbons such as chloroform, carbon tetrachloride, methylene chloride, dichloroethane, trichloroethane, n-hexane, and cyclohexane; ethers such as diethyl ether, dioxane, and tetrahydrofuran; ketones such as acetone, methyl ethyl ketone, and methyl isobutyl ketone; nitriles such as acetonitrile and propionitrile; and aprotic polar solvents such as dimethylformamide, N-methylpyrrolidone, dimethyl sulfoxide, and sulfolane. Examples of the acid acceptor which can be used in the Reaction (A) above include alkali metal hydroxides such as sodium hydroxide and potassium hydroxide; alkali metal or alkaline earth metal carbonates such as anhydrous potassium carbonate and anhydrous calcium carbonate; alkali metal hydrides such as sodium hydride; inorganic bases such as alkali metals, e.g., metallic sodium; and organic bases such as triethylamine.

The foregoing Reaction (B) is a reversible reaction, and if the heating is carried out while removing off the formed $R^4.H$, the desired compound (II-2) can be obtained. Further, as the alkoxy group for $R^{2'}$ and $R^{3'}$ in the same reaction, a methoxy group or an ethoxy group is particularly preferred.

A compound represented by formula (IV) wherein Y represents a chlorine atom or a bromine atom can be prepared by the following Reaction Scheme (7).

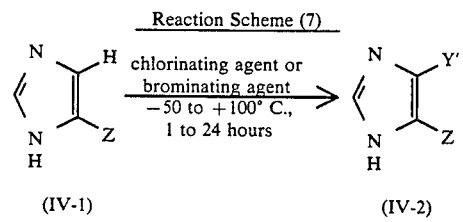

In the Reaction Scheme (7), Y' represents a chlorine atom or a bromine atom, and Z is the same as defined above.

The reaction of the Reaction Scheme (7) is carried out, if necessary and desired, in the presence of a diluent and a neutralizing agent as described above.

The compounds represented by formula (IV-1) are known or can be prepared in the method described in European Patent 298196A.

In the Reaction Scheme (1), the imidazole compound represented by formula (I-3) can be, for example, derived into the compound represented by formula (III) by the following Reaction Scheme (8). The compound represented by formula (III) exhibits excellent effects as a biocide for controlling harmful organisms in the agricultural and horticultural areas, as described later.

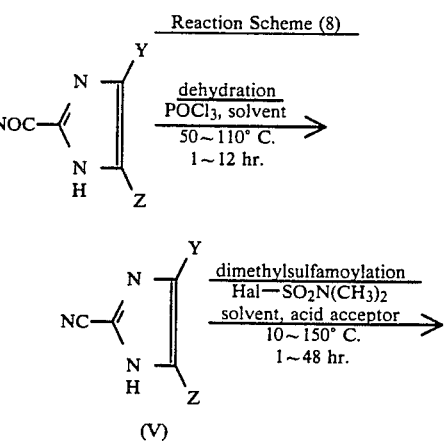

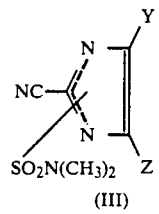

In the Reaction Scheme (8), Hal means a halogen atom, and Y and Z are the same as defined above. Examples of the halogen atom include a fluorine atom, a chlorine atom, a bromine atom, and an iodine atom. As the solvent used in the dehydration and as the solvent and the acid acceptor used in the dimethylsulfamoylation, the same solvent and acid acceptor used in the Reaction (A) of the Reaction Scheme (6) can be used. In the dehydration, organic bases such as pyridine may be used. Further, phosphorus oxychloride (POCl₃) used as the dehydrating agent can be replaced by trichloroacetic anhydride, trichloroacetonitrile, trichloroacetyl chloride, oxalyl chloride, thionyl chloride, acetic anhydride, phosphorus trichloride, phosphorus pentoxide, phosphonitrilic chloride, phosgene (dimers), cyanuric chloride, titanium tetrachloride, or formic acid.

In the compound represented by formula (V) in the Reaction Scheme (8), in the case that Y in formula (V) represents a hydrogen atom, if desired, a reaction with a chlorinating agent or a brominating agent is carried out at −50° to +100° C. for 1 to 24 hours, whereby the compound can be converted into a compound wherein Y represents a chlorine atom or a bromine atom. This compound can further be derived into the compound represented by formula (III) upon dimethylsulfamoylation.

Among the compounds represented by the foregoing formulae, the compound represented by formula (I) means the following compound:

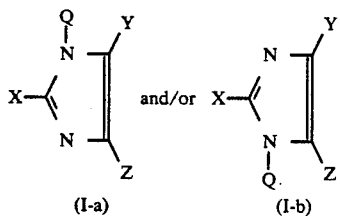

(I-a)    (I-b)

the compound represented by formula (II) means the following compound:

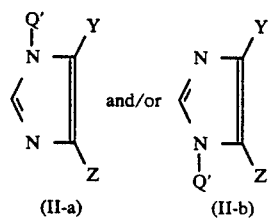

(II-a)    (II-b)

and the compound represented by formula (III) means the following compound:

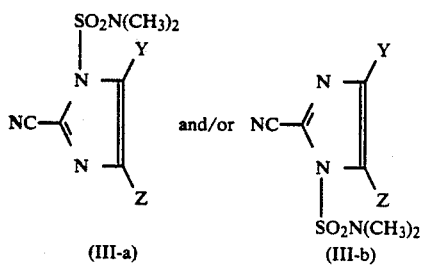

(III-a)    (III-b)

In the compound represented by formula (IV), there is a tautomer as expressed below:

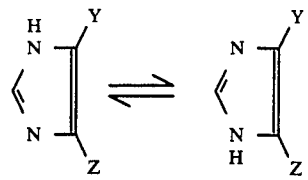

Further, in the compound represented by formula (V), there is a tautomer as expressed below.

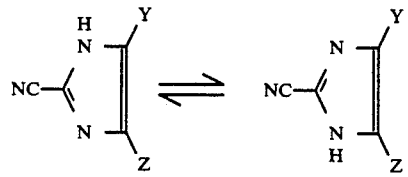

In the foregoing formulae, X, Y, Z, Q and Q' are the same as defined above.

Accordingly, in the case that the compound represented by formula (II) is produced using the compound represented by formula (IV) as a starting material, the compound represented by formula (II-a) and/or the compound represented by formula (II-b) are/is obtained. In the case that the compound represented by formula (I) is produced using the compound represented by formula (II-a) and/or the compound represented by formula (II-b) as a starting material(s), the compound represented by formula (I-a) and/or the compound represented by formula (I-b) are/is obtained corresponding to the starting material(s). However, in the case that Q represents a hydrogen atom, the compound represented by formula (I-a) and the compound represented by formula (I-b) are a tautomer each other.

Similarly, in the case that the compound represented by formula (III) is produced using, as a starting material, the compound represented by formula (V) where a tautomer is present, the compound represented by formula (III-a) and/or the compound represented by formula (III-b) are/is obtained.

Originating from the reaction for introducing a dimethylsulfamoyl group into the starting material where a tautomer is present, a mixture of two kinds of isomers or either isomer is obtained. Whether a mixture of two kinds of isomers or either isomer is obtained is determined depending upon the kind of starting material, the type of reaction for obtaining a desired product from a starting material, and the respective reaction conditions, etc.. In the case that the mixture is obtained, its mixing ratio is determined in a similar fashion.

SYNTHESIS EXAMPLE 1

Synthesis of 1-Dimethylsulfamoyl-2-(ethoxycarbonyl)-4(5)-phenylimidazole (Compound No. 1) and 2-(Ethoxycarbonyl)-4(5)-phenylimidazole (Compound No. 2)

[1] 23.04 g of 4(5)-phenylimidazole obtained by heating phenacyl chloride together with an excess of formamide at 140° to 160° C. was dissolved in 320 ml of acetone, and 12.14 g of anhydrous potassium carbonate was added to the solution, followed by refluxing the mixture upon heating for 2 hours. After cooling, 45 ml of an acetone solution containing 25.25 g of dimethylsulfamoyl chloride was added dropwise to the resulting mixture, and after completion of the dropwise addition, the mixture was further refluxed upon heating for an additional 4.5 hours to complete the reaction.

After completion of the reaction, the reaction mixture was cooled, solids were removed by filtration, the solvent was evaporated off under reduced pressure, and the residue was purified by silica gel column chromatography (developing solvent: methylene chloride). There was thus obtained 17.8 g of 1-dimethylsulfamoyl-4(5)-phenylimidazole having a melting point of 96° to 100° C.

[2] 25 g of 1-dimethylsulfamoyl-4(5)-phenylimidazole obtained in the same manner as in Step [1] above was dissolved in 300 ml of tetrahydrofuran, and the solution was cooled to −70° C. under a nitrogen atmosphere, followed by adding dropwise thereto 70 ml of a 1.6 M n-butyl lithium hexane solution over 30 minutes. After completion of the dropwise addition, the mixture was stirred at −70° C. for 30 minutes, and 12 g of ethyl chloroformate was added dropwise to the resulting mixture. After completion of the dropwise addition, the mixture was reacted under stirring for 15 hours, while gradually elevating the temperature to room temperature.

After completion of the reaction, the reaction mixture was poured into water and then extracted with ethyl acetate. The extract was washed with water and dried over anhydrous sodium sulfate, the solvent was evaporated off under reduced pressure, and the residue was purified by silica gel column chromatography (developing solvent: methylene chloride). There was thus obtained 30 g of semisolid 1-dimethylsulfamoyl-2-(ethoxycarbonyl)-4(5)-phenylimidazole (Compound No. 1).

[3] 24 g of 1-dimethylsulfamoyl-2-(ethoxycarbonyl)-4(5)-phenylimidazole obtained in Step [2] above was dissolved in 240 ml of ethanol, and the solution was reacted with 15 ml of concentrated hydrochloric acid at a reflux temperature for one hour.

After completion of the reaction, the reaction mixture was poured into water, neutralized with ammonia water, and then extrated with methylene chloride. After evaporating off the solvent under reduced pressure, there was obtained 10 g of 2-(ethoxycarbonyl)-4(5)-phenylimidazole (Compound No. 2) having a melting point of 129° to 132° C.

[4] In a 100 ml autoclave, 2.16 g of 2-(ethoxycarbonyl)-4(5)-phenylimidazole obtained in Step [3] above, 20 ml of 28% ammonia water, and 40 ml of ethanol were charged and reacted at 80° to 90° C. for 4 hours.

After completion of the reaction, the reaction mixture was cooled, the solvent was evaporated off under reduced pressure, and the residue was poured into water. A precipitated solid was filtered out, washed successively with water and n-hexane, and then dried to obtain 1.5 g of 2-carbamoyl-4(5)-phenylimidazole having a melting point of 214° to 215° C.

REFERENTIAL SYNTHESIS EXAMPLE 1

Steps for Production of Final Product

[A] When 2-carbamoyl-4(5)-phenylimidazole obtained in Step [4] of Synthesis Example 1 is subjected to dehydration reaction with phosphorus oxychloride or the like at 90° to 100° C., 2-cyano-4(5)-phenylimidazole (melting point: 203° to 205° C.) can obtained.

[B] 1.352 g of 2-cyano-4(5)-phenylimidazole obtained in Step [A] above was dissolved in 100 ml of chloroform, and 1.175 g of N-chlorosuccinimide was added to the solution, followed by reacting the mixture under reflux conditions upon heating for 4 hours.

After completion of the reaction, the reaction mixture was poured into water and extracted with chloroform. The extract was washed with water and dried over anhydrous sodium sulfate, the solvent was evaporated off under reduced pressure, and the residue was purified by silica gel column chromatography (developing solvent: methylene chloride). There was thus obtained 1.28 g of 4(5)-chloro-2-cyano-5(4)-phenylimidazole having a melting point of 149° to 151° C.

[C] 0.43 g of 4(5)-chloro-2-cyano-5(4)-phenylimidazole obtained in Step [B] above was dissolved in 6 ml of acetone, and 0.29 g of anhydrous potassium carbonate and 0.36 g of dimethylsulfamoyl chloride were added to the solution, followed by reacting the mixture under reflux conditions upon heating for 30 minutes.

After completion of the reaction, the reaction mixture was poured into water and extracted with ethyl acetate. The extract was washed with water and dried over anhydrous sodium sulfate, the solvent was evaporated off under reduced pressure, and the residue was purified by silica gel column chromatography (developing solvent: methylene chloride). There was thus obtained 0.5 g of 4(5)-chloro-2-cyano-1-dimethylsulfamoyl-5(4)-phenylimidazole having a melting point of 106° to 109° C.

The results of an NMR spectral analysis revealed that this compound was an isomer mixture of 4-chloro-2-cyano-1-dimethylsulfamoyl-5-phenylimidazole and 5-chloro-2-cyano-1-dimethylsulfamoyl-4-phenylimidazole in a substantially equal proportion.

[D] 2.9 g of the isomer mixture obtained in the same manner as in Step [C] above was allowed to stand at room temperature for 24 hours and purified by silica gel column chromatography using methylene chloride as a developing solvent, to obtain 1.15 g of 4-chloro-2-cyano-1-dimethylsulfamoyl-5-phenylimidazole (Compound A) having a melting point of 109° to 112° C. By this purification and separation, there was also obtained 0.7 g of 4(5)-chloro-2-cyano-5(4)-phenylimidazole.

SYNTHESIS EXAMPLE 2

Synthesis of 2-(Ethoxycarbonyl)-4(5)-phenylimidazole (Compound No. 2)

3.55 g of ethyl 2-thiooxamate was dissolved in 50 ml of methylene chloride in a nitrogen atmosphere. To this solution was added dropwise 40 ml of a 1 M methylene chloride solution of triethyloxonium tetrafluoroborate at room temperature over 4 hours. After completion of the dropwise addition, the mixture was reacted under stirring for an addition 2 hours. Thereafter, the methylene chloride was evaporated off under reduced pressure, and the residue was mixed with 30 ml of acetic acid, 4.6 g of phenacylamine hydrochloride (inclusive of a hydrobromide, which was obtained by reacting phenacyl bromide and hexamethylenetetramine in chloroform and further reacting the reaction mixture with concentrated hydrochloric acid in ethanol; melting point: 185° C.), and 4.4 g of sodium acetate, followed by reacting the mixture at 90° to 100° C. for 3 hours.

After allowing the reaction mixture to stand for cooling, the inorganic salt was separated out, and the acetic acid was evaporated off under reduced pressure. The residue was purified by silica gel column chromatography (developing solvent: methylene chloride) to obtain 2.9 g of the titled compound having a melting point of 122° to 131° C.

SYNTHESIS EXAMPLE 3

Synthesis of
4-Chloro-1-dimethylsulfamoyl-2-(ethoxycarbonyl)-5-phenylimidazole (Compound No. 4-b),
4(5)-Chloro-2-(ethoxycarbonyl)-5(4)-phenylimidazole (Compound No. 5) and
2-Carbamoyl-4(5)-chloro-5(4)-phenylimidazole (Compound No. 6)

4(5)-Chloro-1-dimethylsulfamoyl-5(4)-phenylimidazole (melting point: 100° to 110° C.) was obtained in the same manner as in Step [1] of Synthesis Example 1, except for using 4(5)-chloro-5(4)-phenylimidazole (melting point: 232° to 235° C.) obtained by chlorinating 4(5)-phenylimidazole with N-chlorosuccinimide in chloroform upon heating. After heating, the resulting product was purified and separated to obtain 4-chloro-1-dimethylsulfamoyl-5-phenylimidazole which was then treated in the same manner as in Step [2] of Synthesis Example 1. There was thus obtained 4-chloro-1-dimethylsulfamoyl-2-(ethoxycarbonyl)-5-phenylimidazole (Compound No. 4-b) having a melting point of 97° to 100° C. From this compound can be obtained 4(5)-chloro-2-(ethoxycarbonyl)-5(4)-phenylimidazole having a melting point of 133° to 135° C. in the same manner as in Step [3] of Synthesis Example 1, from which 2-carbamoyl-4(5)-chloro-5(4)-phenylimidazole (Compound No. 6) having a melting point of 275° to 277° C. can further be obtained in the same manner as in Step [4] of Synthesis Example 1.

REFERENTIAL SYNTHESIS EXAMPLE 2

Step for Production of Final Product

A mixture of 2 g of 2-carbamoyl-4(5)-chloro-5(4)-phenylimidazole (Compound No. 6) as obtained above and 13.8 g of phosphorus oxychloride was gradually heated and reacted at 100° C. for one hour.

After completion of the reaction, the excessive phosphorus oxychloride was evaporated off under reduced pressure, and the residue was added with water and neutralized with ammonia water. Thereafter, the resulting mixture was extracted with ethyl acetate and washed with water, and the solvent was evaporated off to obtain 1.66 g of 4(5)-chloro-2-cyano-5(4)-phenylimidazole having a melting point of 149° to 151° C. From this compound can be obtained 4-chloro-2-cyano-1-dimethylsulfamoyl-5-phenylimidazole (Compound A) in the same manners as in Steps [C] and [D] of Referential Synthesis Example 1.

SYNTHESIS EXAMPLE 4

Synthesis of
4(5)-Chloro-5(4)-(3-chloropropyl)-1-dimethylsulfamoyl-2-(ethoxycarbonyl)imidazole (Compound No. 7),
2-Carbamoyl-4(5)-chloro-5(4)-(3-chloropropyl)imidazole (Compound No. 8),
4(5)-Chloro-5(4)-(3-chloropropyl)-2-(ethoxycarbonyl)imidazole (Compound No. 9) and
2-Carbamoyl-4(5)-chloro-5(4)-(3-chloropropyl)-1-dimethylsulfamoylimidazole (Compound No. 10)

[1] 4,5-Dichloroimidazole was reacted with chloromethyl methyl ether to obtain 4,5-dichloro-1-methoxymethylimidazole ($n_D^{26.8}$:1.5090). This compound was gradually crystallized after being allowed to stand (melting point: 41° to 44° C.).

Into a four-necked flask were charged 20 g of 4,5-dichloro-1-methoxymethylimidazole and 200 ml of dry tetrahydrofuran in a nitrogen atmosphere, and 70 ml of a 1.6 M n-butyl lithium hexane solution was gradually added dropwise thereto while keeping the system at −70° C. or lower using dry ice-acetone. After completion of the dropwise addition, the mixture was kept at the same temperature for 30 minutes, and thereafter, 13 g of trimethylchlorosilane was added dropwise thereto at −70° C. or lower. After completion of the dropwise addition, the resulting mixture was stirred overnight and then gradually returned to room temperature. After evaporating off the solvent under reduced pressure, 200 ml of dry tetrahydrofuran was added to the residue in a nitrogen atmosphere, and 70 ml of a 1.6 M n-butyl lithium hexane solution was gradually added dropwise thereto while keeping the system at −70° C. or lower using dry ice-acetone. After completion of the dropwise addition, the mixture was kept at the same temperature for 30 minutes, and thereafter, 27 g of 1-chloro-3-iodopropane was added dropwise thereto at −70° C. or lower. After completion of the dropwise addition, the resulting mixture was stirred overnight and then gradually returned to room temperature to thereby complete the reaction.

After completion of the reaction, the solvent was evaporated off under reduced pressure, and the residue was poured into water. After adding thereto dilute hydrochloric acid, the mixture was stirred at room temperature for 30 minutes and extracted with methylene chloride. The methylene chloride layer was washed with water and dried over anhydrous sodium sulfate. After drying, the methylene chloride was evaporated off to obtain 23 g of 4-chloro-5-(3-chloropropyl)-1-methoxymethylimidazole as an oily substance.

[2] 23 g of 4-chloro-5-(3-chloropropyl)-1-methoxymethylimidazole obtained in Step [1] above was reacted with 15 ml of concentrated hydrochloric acid and 120 ml of ethanol for 5 hours under reflux conditions.

After completion of the reaction, the reaction mixture was poured into water and washed with methylene chloride. The aqueous layer was made alkaline with potassium carbonate, and a precipitated solid was filtered out, washed with water and then dried to obtain 7.5 g of 4(5)-chloro-5(4)-(3-chloropropyl)imidazole having a melting point of 148° to 150° C.

[3] 7.5 g of 4(5)-chloro-5(4)-(3-chloropropyl)imidazole obtained in Step [2] above wa dissolved in 100 ml of anhydrous acetonitrile, and 5.7 g of anhydrous potassium carbonate and 6.5 g of dimethylsulfamoyl chloride were added to the solution, followed by reacting the mixture at room temperature for 18 hours.

After completion of the reaction, the reaction mixture was poured into water and extracted with ethyl acetate, and the ethyl acetate layer was washed with water and dried over anhydrous sodium sulfate. After evaporating off the solvent under reduced pressure, the residue was purified by silica gel column chromatography (developing solvent : methylene chloride) to obtain 3.8 g of 4(5)-chloro-5(4)-(3-chloropropyl)-1-dimethylsulfamoylimidazole having a melting point of 104° to 106° C. The NMR analysis revealed that this compound was substantially 4-chloro-5-(3-chloropropyl)-1-dimethylsulfamoylimidazole. Further, 2.5 g of 4(5)-chloro-5(4)-(3-chloropropyl)imidazole was also recovered.

[4] 3 g of 4(5)-chloro-5(4)-(3-chloropropyl)-1-dimethylsulfamoylimidazole obtained in the same manner as in Step [3] above was dissolved in 50 ml of tetrahydrofuran, the solution was cooled to −70° C. in a nitrogen atmosphere, and 6.7 ml of a 1.6 M n-butyl lithium hexane solution was added dropwise thereto over 3 minutes. After completion of the dropwise addition, the mixture was stirred at −70° C. for 30 minutes, and 3 ml of a tetrahydrofuran solution containing 1.1 g of ethyl chloroformate was added dropwise thereto. After completion of the dropwise addition, the resulting mixture was reacting with stirring for 15 hours while gradually elevating the temperature to room temperature.

After completion of the reaction, the reaction mixture was poured into water and extracted with methylene chloride. The extract was washed with water and dried over anhydrous sodium sulfate, the solvent was evaporated off under reduced pressure, and the residue was purified by silica gel column chromatography (developing solvent: methylene chloride). There was thus obtained 4(5)-chloro-5(4)-(3-chloropropyl)-1-dimethylsulfamoyl-2-(ethoxycarbonyl)imidazole (Compound No. 7) having a melting point of from 71° to 74° C. The NMR analysis revealed that this compound was substantially 4-chloro-5-(3-chloropropyl)-1-dimethylsulfamoyl-2-(ethoxycarbonyl) imidazole.

[5] In a 100 ml autoclave, 2 g of 4(5)-chloro-5(4)-(3-chloropropyl)-1-dimethylsulfamoyl-20(ethoxycarbonyl)imidazole obtained in Step [4] above, 20 ml of 28% ammonia water, and 40 ml of ethanol were charged and reacted at 80° to 90° C. for 4 hours.

After completion of the reaction, the reaction mixture was cooled, the solvent was evaporated off under reduced pressure, and the residue was poured into water. A precipitated solid was filtered out, washed successively with water and n-hexane, and then dried to obtain 2-carbamoyl-4(5)-chloro-5(4)-(3-chloropropyl)imidazole (Compound No. 8) having a melting point of 247° to 251° C.

It is considered that in this step, the two reactions simultaneously proceeded, whereby the above-described Compound No. 8 was formed via 4(5)-chloro-5(4)-(3-chloropropyl)-2-(ethoxycarbonyl)imidazole (Compound No. 9), 2-carbamoyl-4(5)-chloro-5(4)-(3-chloropropyl)-1-dimethylsulfamoylimidazole (Compound No. 10) and the like.

REFERENTIAL SYNTHESIS EXAMPLE 3

Steps for Production of Final Product

[A] When 2-carbamoyl-4(5)-chloro-5(4)-(3-chloropropyl)imidazole obtained in Step [5] of Synthesis Example 4 is subjected to dehydration reaction with phosphorus oxychloride or the like at 90° to 100° C., 4(5)-chloro-5(4)-(3-chloropropyl)-2-cyanoimidazole (melting point: 117° to 120° C.) can obtained.

[B] From 4(5)-chloro-5(4)-(3-chloropropyl)-2-cyanoimidazole obtained in Step [A] above can be obtained 4(5)-chloro-5(4)-(3-chloropropyl)-2-cyano-1-dimethylsulfamoylimidazole having a melting point of 87° to 92° C., from which can further be obtained 4-chloro-5-(3-chloropropyl)-2-cyano-1-dimethylsulfamoylimidazole (Compound B) having a melting point of 106° to 110° C., in the same manners as in Steps [C] and [D] of Referential Synthesis Example 1.

SYNTHESIS EXAMPLE 5

Synthesis of 4(5)-(3-Chloropropyl)-2-(ethoxycarbonyl)imidazole (Compound No. 11) and 2-Carbamoyl-4(5)-(3chloropropyl)imidazole (Compound No. 12)

[1] 24.1 g of 5-chloro-2-pentanone was dissolved in 120 ml of methanol, and 32 g of bromine was added dropwise to the solution at 0° to 5° C. over one hour. After completion of the dropwise addition, the mixture was stirred at 10° C. for 2 hours, and 60 ml of water was added thereto, followed by reacting the resulting mixture at room temperature for 15 hours.

After completion of the reaction, the reaction mixture was poured into 180 ml of water and extracted with methylene chloride, and the extract was dried over anydrous sodium sulfate. The solvent was evaporated off under reduced pressure, and the residue was purified by silica gel column chromatography (developing solvent: methylene chloride) to obtain 34 g of an oily substance. The NMR analysis revealed that this substance was a mixture of 1-bromo-5-chloro-2-pentanone and 3-bromo-5-chloro-2-pentanone in a substantially equal proportion.

[2] A mixture consisting of 33.9 g of the mixture obtained in Step [1] above, 31.45 g of potassium phthalimide and 100 ml of benzene was refluxed upon heating for 10 hours.

After completion of the reaction, the reaction mixture was cooled, and a precipitated solid was filtered out. The solid was thoroughly washed with benzene, and the filtrate and the washing were gathered, and the resulting benzene solution was added with n-hexane. A precipitated solid was collected by filtration to obtain 6.9 g of N-(5-chloro-2-oxopentyl)phthalimide having a melting point of 133° to 134° C.

[3] A mixture consisting of 6.64 g of N-(5-chloro-2-oxopentyl)phthalimide obtained in Step [2] above, 34 ml of concentrated hydrochloric acid, 34.5 ml of water and 24 ml of acetic acid was refluxed upon heating for 10 hours.

After completion of the reaction, the solvent was evaporated off under reduced pressure, and 26 ml of water was added to the residue. The mixture was heated at 70° to 80° C. for 5 minutes and then cooled to room temperature. Precipitated phthalic acid was removed by filtration, and the filtrate was evaporated off under reduced pressure. Ethanol was added to the residue to thereby remove a slight amount of water by azeotropy with ethanol. The residue was dissolved in 30 ml of ethanol, and 240 ml of diethyl ether was added to the ethanol solution. A precipitated solid was collected by filtration to obtain 2.2 g of 1-amino-5-chloro-2-pentanone hydrochloride having a melting point of 100° to 103° C.

[4] 1.62 g of ethyl 2-thiooxamate was dissolved in 23 ml of methylene chloride in a nitrogen atmosphere. To this solution, 18.3 ml of a 1 M methylene chloride solution of triethyloxonium tetrafluoroborate was added dropwise at room temperature over 2 hours. After completion of the dropwise addition, the mixture was reacted with stirring at room temperature for 2 hours. Then, the methylene chloride was evaporated off under reduced pressure, and the residue was mixed with 14 ml of acetic acid, 2.1 g of 1-amino-5-chloro-2-pentanone hydrochloride obtained in Step [3] above and 2 g of sodium acetate, followed by reacting the mixture at 90° to 100° C. for 3 hours. After completion of the reaction, the reaction mixture was cooled, an inorganic salt was filtered off, and the acetic acid was evaporated off under reduced pressure. The residue was purified by silica gel column chromatography (developing solvent: a mixed (1:3) solvent of ethyl acetate and methylene chloride) to obtain 0.56 g of 4(5)-(3-chloropropyl)-2-(ethoxycarbonyl)imidazole (Compound No. 11) having a melting point of 69° to 72° C.

[5] 2-Carbamoyl-4(5)-(3-chloropropyl)imidazole (Compound No. 12) can be obtained from 4(5)-(3-chloropropyl)-2-(ethoxycarbonyl)imidazole (Compound No. 11) obtained in Step [4] above, in the same manner as in Step [5] of Synthesis Example 4.

REFERENTIAL SYNTHESIS EXAMPLE 4

Step for Production of Final Product

When 2-carbamoyl-4(5)-(3-chloropropyl)imidazole (Compound No. 12) obtained in Step [5] of Synthesis Example 5 is subjected to dehydration reaction with phosphorus oxychloride or the like at 90° to 100° C., 4(5)-(3-chloropropyl)-2-cyanoimidazole (melting point: 102° to 105° C.) can be obtained. Further, when this compound is chlorinated with N-chlorosuccinimide in methanol, 4(5)-chloro-5(4)-(3-chloropropyl)-2-cyanoimidazole (melting point: 117° to 120° C.) is obtained. Then, from this compound can be obtained 4-chloro-5-(3-chloropropyl)-2-cyano-1-dimethylsulfamoylimidazole (Compound B) in the same manners as in Steps [C] and [D] of Referential Synthesis Example 1.

SYNTHESIS EXAMPLE 6

Synthesis of 2-(Ethoxycarbonyl)-4(5)-phenylimidazole (Compound No. 2)

A hydrogen chloride gas was introduced into a diethyl ether solution of an equimolar mixture of ethyl cyanoformate and ethanol at 0° C. or lower, and a precipitated crystal was filtered out and washed with diethyl ether to obtain ethyl ethoxycarbonylformimidate hydrochloride [$H_5C_2O_2CC(OC_2H_5)=NH.HCl$]. 5.4 g of this hydrochloride, 40 ml of acetic acid, 5.0 g of phenacylamine hydrochloride (the same as used in Synthesis Example 2) and 4.85 g of anhydrous sodium acetate were mixed and reacted with stirring at 90° to 100° C. for 4 hours.

After cooling, an inorganic salt was filtered off, and the acetic acid was evaporated off under reduced pressure. The residue was purified by silica gel column chromatography (developing solvent: methylene chloride) to obtain 3.52 g of the titled compound (Compound No. 2) having a melting point of 128° to 131° C.

SYNTHESIS EXAMPLE 7

Synthesis of 2-(Ethoxycarbonyl)-4(5)-phenylimidazole (Compound No. 2)

4.0 g of ethyl 2-thiooxamate was dissolved in 70 ml of methylene chloride in a nitrogen atmosphere. To this solution, 5.2 g of ethyl iodide was added dropwise at room temperature. After completion of the dropwise addition, the mixture was reacted with stirring for an additional 5 hours to obtain ethyl ethoxycarbonylformthioimidate hydrogen iodide [$H_5C_2O_2CC(SC_2H_5)=NH.HI$]. Then, the methylene chloride was evaporated off under reduced pressure, and the residue was mixed with 35 ml of acetic acid, 4.9 g of anhydrous sodium acetate and 5.2 g of phenacylamine hydrochloride (the same as used in Synthesis Example 2), followed by reacting the mixture at 90° to 100° C. for 3 hours.

After allowing to stand the reaction mixture for cooling, an inorganic salt was filtered off, and the acetic acid was evaporated off under reduced pressure. The residue was purified by silica gel column chromatography (developing solvent: methylene chloride) to obtain 2.9 g of the titled compound (Compound No. 2) having a melting point of 128° to 131° C.

SYNTHESIS EXAMPLE 8

Synthesis of 4(5)-Chloro-2-(ethoxycarbonyl)-5(4)-phenylimidazole (Compound No. 5)

2.16 g of 2-(ethoxycarbonyl)-4(5)-phenylimidazole (Compound No. 2) and 1.6 g anhydrous sodium acetate were dissolved in 30 ml of acetic acid. 5 ml of acetic acid containing 0.7 g of chlorine gas was added dropwise to the solution at room temperature over 2 to 3 minutes. After completion of the dropwise addition, the mixture was reacted with stirring for an additional 18 hours.

After completion of the reaction, the reaction mixture was poured into water, and a precipitated crystal was filtered out, washed with water and then dried to obtain 2 g of the titled compound (Compound No. 5).

SYNTHESIS EXAMPLE 9

Synthesis of 4(5)-Chloro-5(4)-phenylimidazole-2-carboxylic acid (Compound No. 15)

2.5 g of 4(5)-chloro-2-(ethoxycarbonyl)-5(4)-phenylimidazole (Compound No. 5) was added to 50 ml of a 5% aqueous sodium hydroxide solution, and the mixture was reacted at the reflux temperature for one hour to obtain a reaction mixture including sodium 4(5)-chloro-5(4)-phenylimidazole-2-carboxylate.

The reaction mixture was poured into ice water and neutralized with hydrochloric acid. A precipitated crystal was separated by filtration and washed with water to obtain 4(5)-chloro-5(4)-phenylimidazole-2-carboxylic acid (Compound No. 15) having a melting point of 158° to 160° C.

REFERENTIAL SYNTHESIS EXAMPLE 5

Steps for Production of Final Product

Compound No. 15 can be derived into useful 2-cyanoimidazole compounds in the methods known in the art. For example, according to the reactions described in Recl. Trav. Chim. Pays-Bas, 92(3), 449–459 (1973), Compound No. 15 can be reacted with thionyl chloride to obtain an active intermediate (an acid chloride or a dimer form of a tricylic compound containing pyrazine), and the active intermediate can be reacted with ammonia to obtain 2-carbamoyl-4(5)-chloro-5(4)-phenylimidazole (Compound No. 6) which can further be reacted with phosphorous oxychloride to obtain 4(5)-chloro-2-cyano-5(4)-phenylimidazole. Then, 4-chloro-2-cyano-1-dimethylsulfamoyl-5-phenylimidazole (Compound A) can be obtained from 4(5)-chloro-2-cyano-5(4)-phenylimidazole in the same manner as in Steps [C] and [D] of Referential Example 1.

Typical examples of the imidazole compound according to the present invention are shown in Table 1.

TABLE 1

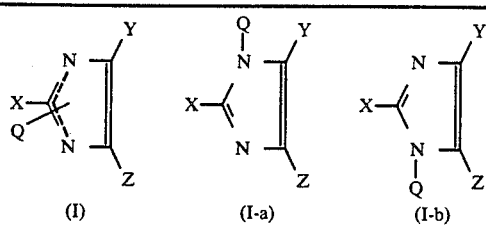

(I)  (I-a)  (I-b)

| Compound No. | X | Y | Z | Q | Physical Properties |
|---|---|---|---|---|---|
| 1 | —COOC$_2$H$_5$ | H | phenyl | —CO$_2$N(CH$_3$) | semisolid |
| 2 | —COOC$_2$H$_5$ | H | phenyl | H | m.p.: 129–132° C. |
| 3 | —CONH$_2$ | H | 4-methyl-phenyl | H | m.p.: 236–240° C. |
| 4-b | —COOC$_2$H$_5$ | Cl | phenyl | —SO$_2$N(CH$_3$)$_2$ | m.p.: 97–100° C. |
| 5 | —COOC$_2$H$_5$ | Cl | phenyl | H | m.p.: 133–135° C. |
| 6 | —CONH$_2$ | Cl | phenyl | H | m.p.: 275–277° C. |
| 7 | —COOC$_2$H$_5$ | Cl | 3-chloro-propyl | —SO$_2$N(CH$_3$)$_2$ | m.p.: 71–74° C. |
| 8 | —CONH$_2$ | Cl | 3-chloro-propyl | H | m.p.: 247–251° C. |
| 9 | —COOC$_2$H$_5$ | Cl | 3-chloro-propyl | H | — |
| 10 | —CONH$_2$ | Cl | 3-chloro-propyl | —SO$_2$N(CH$_3$)$_2$ | — |
| 11 | —COOC$_2$H$_5$ | H | 3-chloro-propyl | H | m.p.: 69–72° C. |
| 12 | —CONH$_2$ | H | 3-chloro-propyl | H | — |
| 13 | —COO-benzyl | Cl | 3-chloro-propyl | H | — |
| 14 | —CONH$_2$ | H | 4-chloro-phenyl | H | — |
| 15 | —COOH | Cl | phenyl | H | m.p.: 158–160° C. |
| 16 | —COOC$_2$H$_5$ | H | ethyl | H | — |
| 17 | —COOC$_2$H$_5$ | H | n-propyl | H | — |
| 18 | —COOC$_2$H$_5$ | H | 4-methyl-phenyl | H | — |
| 19 | —COOC$_2$H$_5$ | H | 4-chloro-phenyl | H | — |
| 20 | —CONH$_2$ | H | ethyl | H | — |
| 21 | —CONH$_2$ | H | n-propyl | H | — |
| 22 | —COOCH$_3$ | H | phenyl | H | — |
| 23 | —COO-benzyl | H | phenyl | H | — |
| 24 | —COOCH$_3$ | Cl | phenyl | H | — |
| 25 | —COO-phenyl | Cl | phenyl | H | — |
| 26 | —COO-benzyl | Cl | phenyl | H | — |
| 27 | —CONH$_2$ | Br | phenyl | H | — |
| 28 | —CONH$_2$ | Cl | 5-fluoro-pentyl | H | — |
| 29 | —COOCH$_3$ | Cl | 3-fluoro-phenyl | H | — |
| 30 | —COO-benzyl | Cl | 4-t-butyl-phenyl | H | — |

Among the compounds shown in Table 1, Compound No. 4-b is a compound represented by formula (I-b), and other compounds are each a mixture of compounds represented by formulae (I-a) and (I-b).

In order to demonstrate usefulness of final products which can be derived from the imidazole compound according to the present invention as an intermediate, Referential Test Example as biocides for controlling harmful organisms in the agricultural and horticultural areas is given below.

REFERENTIAL TEST EXAMPLE

Cucumber (cultivars: Suyo) was cultivated in a polyethylene pot having a diameter of 7.5 cm. When cucumber reached the two-leaf stage, a spore suspension of fungi of downly mildew was spray inoculated. Six hours after the inoculation, 10 ml of a solution containing 125 ppm of each of test compounds was sprayed over cucumber using a spray gun. After keeping the pots in a constant temperature chamber of 22° to 24° C. for 6 days, an area of lesion on the first leaf was investigated, and an index of control was determined by the standards for evaluation described below. The results shown in Table 2 were obtained.

Standards for Evaluation

The controlling effect was determined by visually observing a degree of disease of a test plant and expressed by the following 5 grades of the index of control.

| [Index of Control] | [Degree of Disease] |
|---|---|
| 5: | No lesion is noted at all. |
| 4: | Area of lesions is less than 10% as compared to the non-treated plot. |
| 3: | Area of lesions is less than 40% as compared to the non-treated plot. |
| 2: | Area of lesions is less than 70% as compared to the non-treated plot. |
| 1: | Area of lesions is more than 70% as compared to the non-treated plot. |

TABLE 2

| Test Compound | Index of Control |
|---|---|
| Compound A: 4-Chloro-2-cyano-1-dimethylsulfamoyl-5-phenylimidazole | 5 |
| Compound B: 4-Chloro-5-(3-chloro-propyl)-2-cyano-1-dimethylsulfamoyl-imidazole | 5 |

While the invention has been described in detail and wit reference to specific embodiments thereof, it will be apparent to one skilled in the art that various changes and modifications can be made therein without departing from the spirit and scope thereof.

What is claimed is:

1. An imidazole compound represented by formula (I):

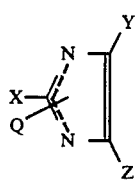

wherein:
X represents a —COOT group, in which T represents a hydrogen atom, an alkyl group, a benzyl group, or a phenyl group; or a —CONH$_2$ group,
Y represents a chlorine atom, or a bromine atom,
Z represents an alkyl group containing from 2 to 6 carbon atoms, which may be substituted with one or more halogen atoms; or a phenyl group which may be substituted with one or more halogen atoms and alkyl groups, and
Q represents a hydrogen atom; an —SO$_2$R$^1$ group, in which R$^1$ represents an alkyl group, a dialkylamino group, or a phenyl group which may be substituted with one or more alkyl groups; or a —CH(R$^2$)(R$^3$) group, in which R$^2$ represents a hydrogen atom, a methyl group, or an alkoxy group, and R$^3$ represents an alkoxy group, an —OCH$_2$CH$_2$Si(CH$_3$)$_3$ group, or a phenyl group which may be substituted with one or more alkyl groups or alkoxy groups.

2. A process for preparing an imiazole compound represented by formula (I-5):

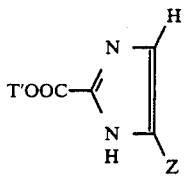

wherein:
Z represents an alkyl group containing from 2 to 6 carbon atoms, which may be substituted with one or more halogen atoms or alkyl groups, and
T' represents an alkyl group containing from 1 to 6 carbon atoms, a benzyl group or a phenyl group,
which process comprises reacting a mineral acid salt of a compound represented by formula (VI):

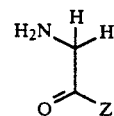

wherein Z is the same as defined above, with a compound represented by formula (VII):

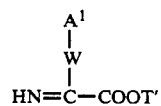

wherein:
T' is the same as defined above,
A$^1$ represents a methyl group or anethyl group, and
W represents an oxygen atom, in the presence of an aliphatic carboxylic acid and an alkali metal or alkaline earth metal salt of an aliphatic carboxylic acid at a temperature of from 50° to 100° C.

* * * * *